United States Patent
Kawasaki (10) Patent No.: US 7,186,217 B2
(45) Date of Patent: Mar. 6, 2007

(54) BIOLOGICAL PHOTOMETER

(75) Inventor: Shingo Kawasaki, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 186 days.

(21) Appl. No.: 10/509,104

(22) PCT Filed: Mar. 3, 2003

(86) PCT No.: PCT/JP03/02429

§ 371 (c)(1),
(2), (4) Date: Sep. 27, 2004

(87) PCT Pub. No.: WO03/084400

PCT Pub. Date: Oct. 16, 2003

(65) Prior Publication Data

US 2005/0177033 A1   Aug. 11, 2005

(30) Foreign Application Priority Data

Mar. 26, 2002 (JP) .............................. 2002-085350

(51) Int. Cl.
*A61B 5/00* (2006.01)
(52) U.S. Cl. ..................... 600/300; 600/309; 600/310
(58) Field of Classification Search ................ 600/322, 600/323, 324, 473, 476; 128/920, 923
See application file for complete search history.

(56) References Cited

U.S. PATENT DOCUMENTS 5,564,418 A * 10/1996 Ozaki et al. ................. 600/323

6,240,309 B1 * 5/2001 Yamashita et al. .......... 600/407

FOREIGN PATENT DOCUMENTS

| JP | 57-115232 | 7/1982 |
|---|---|---|
| JP | 63-275323 | 11/1988 |
| JP | 2000-237194 | 9/2000 |

(Continued)

OTHER PUBLICATIONS

H. Koizumi, et al., "Hikari Topographi ni yoru Mushinshu Koji no Kino Byogha", Seitai no Kagaku, Jun. 15, 1999, vol. 50, No. 3, pp. 236-244.

(Continued)

*Primary Examiner*—Eric Winakur
*Assistant Examiner*—Etsub Berhanu
(74) *Attorney, Agent, or Firm*—Antonelli, Terry, Stout and Kraus, LLP.

(57) ABSTRACT

A biological photometer having, in its signal processing unit, a memory unit in which characteristics of hemoglobin change pattern of healthy case and various diseases are stored as reference template, characteristic extraction unit in which characteristic of hemoglobin change patterns are extracted from hemoglobin signals measured in a photometer unit, and a judgment unit in which the characteristics of the hemoglobin change patterns thus extracted are compared with the reference templates stored in the memory unit so as to judge whether the subject is healthy or ill. As the characteristics of the hemoglobin change pattern, use is made of hemoglobin change pattern curve as well as factors determined therefrom such as latent time, maximum level, time for attaining the maximum level, differential quantitative change, integral quantitative change, etc. Using this biological photometer, various diseases can be easily and quantitatively diagnosed.

32 Claims, 7 Drawing Sheets

FOREIGN PATENT DOCUMENTS

| | | |
|---|---|---|
| JP | 2001-245871 | 9/2001 |
| JP | 2002-177281 | 6/2002 |

OTHER PUBLICATIONS

E. Watanabe, et al., "Clinical Application of Photo Topography" Tokyo Police Hospital, MEDIX vol. 30.

M. Fukuda, et al., "Functional Brain Imaging in Psychiarty Using Multi-Channel Near-Infrared Spectroscopy", Clinical Psychiatry, vol. 30, No. 8, Gunma University Affiliated Hospital.

* cited by examiner

Reference Template

| | Normal Health N | Disease A | Disease B |
|---|---|---|---|
| Average Variation Pattern | $\overline{N}(t)$ | $\overline{A}(t)$ | $\overline{B}(t)$ |
| Latent Time | ・Average : 1sec.<br>・SD : ±0.5 | ・Average : 1.5sec.<br>・SD : ±0.2 | ・Average : 0.5sec.<br>・SD : ±0.1 |
| Maximum | ・Average : 2mMmm<br>・SD : ±0.3 | ・Average : 1mMmm<br>・SD : ±0.3 | ・Average : 1.5mMmm<br>・SD : ±0.5 |
| Time Attaining Maximum | ・Average : 0.5sec.<br>・SD : ±0.1 | ・Average : 1sec.<br>・SD : ±0.2 | ・Average : 0.7sec.<br>・SD : ±0.2 |
| Differential Quantitative Change | ・Average : 4mMmm<br>・SD : ±0.5 | ・Average : 1mMmm<br>・SD : ±0.3 | ・Average : 1.8mMmm<br>・SD : ±0.2 |
| Integral Quantitative Change | ・Average : 8mMmm<br>・SD : ±2.4 | ・Average : 5mMmm<br>・SD : ±1.7 | ・Average : 6mMmm<br>・SD : ±1.9 |

SD: Standard Deviation

BIOLOGICAL PHOTOMETER

FIELD OF THE INVENTION

The present invention relates to a biological photometer, which measures information inside a living body by making use of a light having a wavelength in a region of visual to infrared and in particular, relates to a biological photometer which permits to diagnoses efficiently normal health or any one of diseases of a subject by making use of information of density change of hemoglobin in a living body.

BACKGROUND ART

A biological photometer is an instrument, which permits to measure simply and easily blood circulation, blood circulation dynamics and hemoglobin variation in blood inside a living body with a low restriction to a subject. As such a biological photometer, for example, JP-A-57-115232 and JP-A-63-275323 disclose instruments in which a light having a wavelength in a region of visual to infrared is irradiated into a living body and a light transmitted inside the living body or a light reflected near the surface of the living body are detected to measure the above referred to information inside the living body. With these instruments, through irradiating light from a plurality of points as well as detecting light from a plurality of points near the irradiation points, information inside the living body in the region covered by these points can be obtained. A graph displaying a hemoglobin variation in the covered region in a form of a map is called as topography and a clinical application of the topography is expected and is now being reduced into practice.

As a clinical application of a biological photometer, for example, in a case when a head portion is the measurement object, local focus identification during epileptic seizure and diagnosis of hypo function in melancholia and integration dysfunction syndrome (schizophrenia) due to hemoglobin variation inside the brain are enumerated. More specifically, it is confirmed by making use of a biological photometer that at the beginning of epileptic seizure a steep hemoglobin variation occurs (WATANABE Eiju et al. Tokyo Police Hospital "Clinical Application of Photo Topography" MEDIX Vol. 30). Further, it is reported that in connection with melancholia and schizophrenia an abnormality in a hemoglobin variation pattern at the frontal lobe occurs (FUKUDA Masato et al. "Functional Brain Imaging in Psychiatry Using Multi-Channel Near-Infrared Spectroscopy" Clinical Psychiatry, Vol. 30, No. 8, Gunma University Affiliated Hospital).

However, since a conventional biographical photometer only displays a hemoglobin signal variation obtained from light such as transmitted through a living body and reflected therein in a form of time course graph or topography, a judgment of the above referred to diseases and the like from the displayed graphs has to rely on experiences and requires a high specialization.

SUMMARY OF THE INVENTION

An object of the present invention is to provide a biological photometer which permits to easily diagnose whether normal health or diseases of a subject.

Another object of the present invention is to provide a biological photometer, which incorporates as reference values hemoglobin variation information of normal health and a variety of diseases, which is valuable for diagnosis.

A still another object of the present invention is to provide a biological photometer which permits to compare measurement result with reference-values of normal health and a variety of diseases and to diagnose whether normal health or diseases of a subject.

A biological photometer according to the present invention, which achieves the above objects comprises a light source which generates light being irradiated to a subject, a photometer unit which detects light transmitted inside the subject and produces a hemoglobin signal corresponding to hemoglobin density inside the subject and a signal processing unit which prepares biological information of the subject based on the measured hemoglobin signal and displays the same, and is characterized in that the signal processing unit is provided with a characteristic extraction unit which extracts characteristics of hemoglobin variation patterns of normal health and a variety of diseases based on the hemoglobin signal.

According to the above biological photometer, when the characteristics of hemoglobin variation patterns of normal health and a variety of diseases are already known, through comparing the extracted characteristic of the hemoglobin variation pattern prepared from the measured hemoglobin signal with the already known characteristics, whether the subject which is the measurement object is normal health or any diseases can be diagnosed. Further, when it is already known that the subject suffers to a certain disease, a hemoglobin variation pattern is prepared based on a hemoglobin signal measured from the subject, a characteristic of hemoglobin variation pattern of the certain disease is extracted and the extracted characteristic is added to a data base which can be used to diagnose measurement results thereafter. In particular, when the characteristics of hemoglobin variation patterns of normal health and a variety of diseases extracted by the characteristic extraction unit are stored in a memory unit as reference templates, an automatic diagnosis of a subject can be performed by making use of these reference templates.

Further, a biological photometer according to the present invention comprises a light source which generates light being irradiated to a subject, a photometer unit which detects light transmitted inside the subject and produces a hemoglobin signal corresponding to hemoglobin density inside the subject and a signal processing unit which prepares biological information of the subject based on the hemoglobin signal and displays the same, and is characterized in that the signal processing unit is provided with a memory unit which stores characteristics of hemoglobin variation patterns of normal health and a variety of diseases as reference templates and a judgment unit which extracts characteristics of hemoglobin variation patterns of normal health and a variety of diseases based on the hemoglobin signal produced by the photometer unit and judges a disease of the subject through comparison between the extracted characteristic of hemoglobin variation pattern and the reference templates stored in the memory unit.

According to the above biological photometer, through provision of the reference templates of normal health and a variety of diseases in the memory unit as well as provision of the function of extracting a characteristic of hemoglobin variation pattern corresponding to the reference templates based on the measured hemoglobin signal and comparing the same with the reference templates, disease diagnosis can be performed at the same time when the hemoglobin signal is measured.

In a biological photometer according to the present invention, the characteristics of hemoglobin variation patterns extracted by the characteristic extraction unit or the characteristics of hemoglobin variation patterns stored as the reference templates includes at least one of hemoglobin variation pattern curve, latent time, maximum level, time for attaining the maximum level, differential quantitative change and integral quantitative change determined from the hemoglobin variation patterns, and the judgment unit performs judgment by making use of at least one of these indexes(characteristics).

Through the use of these indexes, a quantitative diagnosis of a subject is enabled and efficiency of diagnosis is enhanced.

BEST MODES FOR CARRYING OUT THE INVENTION

Embodiments of the biological photometer according to the present invention will be explained with reference to the drawings.

Figure 1:
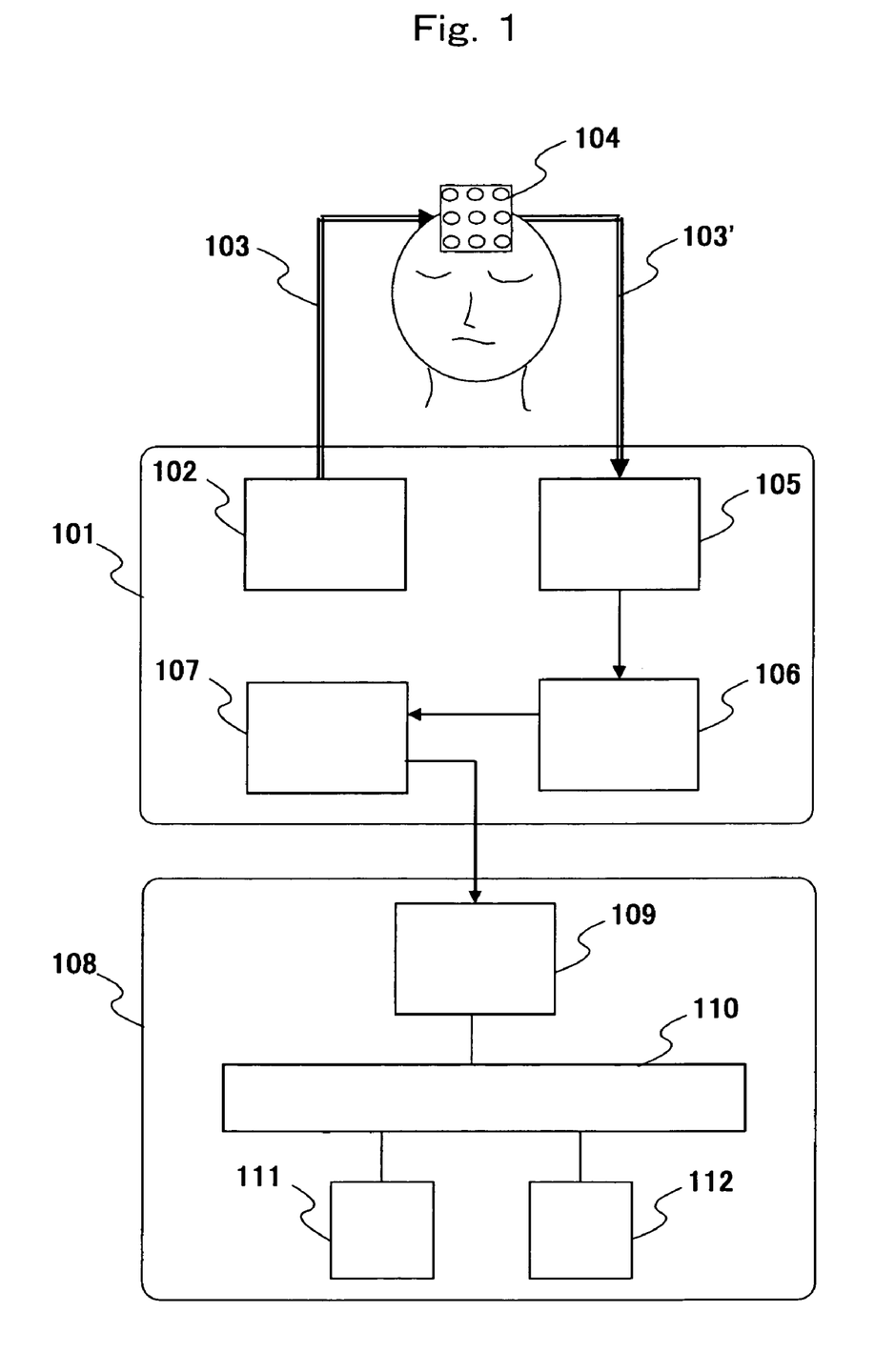
FIG. 1 is a view showing a general outline of a biological photometer according to the present invention.

FIG. 1 is a view showing a general outline of a biological photometer to which the present invention is applied. As shown in the drawing, the biological photometer is primarily constituted by a photo topography unit 101 which irradiates light to a living body as well as detects light transmitted through the subject and a signal processing unit 108 which calculates information inside the living body such as amount (density) of hemoglobin in blood by making use of signals from the photo topography unit 101 and displays the same.

The photo topography unit 101 is constituted by a light source unit 102 for irradiating light having a predetermined wavelength to a detection portion of a subject, a photometer unit 105–107 having light receiving elements which detects light transmitted through the detection portion of the subject or light reflected or scattered at the detection portion (herein below will be called inclusively as transmitted light) and an attachment member 104 which fixes respective ends of optical fiber 103 for transferring the light from the light source unit 102 to the predetermined portion (detection portion) of the subject and optical fiber 103' for transferring the transmitted light from the subject to the photometer unit 105–107 and attaches the same to the subject.

The light source unit 101 is constituted by a plurality of optical modules and each module is provided with two semiconductor lasers for emitting light having a predetermined wavelength in a region from visual to infrared light, for example, light of two wavelengths of 780 nm and 830 nm. Further, the light source unit 101 is provided with an oscillator unit constituted by a plurality of oscillators, each having different oscillation frequency, which provides respectively different modulations to the semiconductor lasers in the respective optical modules.

The lights, for example, of two wavelengths, from the semiconductor lasers are mixed in every optical module and are introduced into one irradiation use optical fiber 103. Although in the drawing only one irradiation use optical fiber 103 is shown, actually, optical fibers 103 as a same number as that of the optical modules are provided. Thereby, lights provided with different modulations for every optical module are irradiated to the surface of the subject from the respective top ends of the plurality of optical fibers.

The top ends of the irradiation use and light receiving use optical fibers 103 and 103' are fixed so that the top ends locate at respective crossing points of a square grid of 3×3 or 4×4 in a manner to alternate each other. A region between a top end of an irradiation use optical fiber 103 and a top end of light receiving use optical fiber 103' assumes a measurement point of the photo measurement.

The photometer unit is provided with photoelectric converting elements 105 such as a photo diode which are connected to the respective light receiving use optical fibers 103' and convert amount (density) of light introduced by the light receiving use optical fibers 103' into corresponding electrical signals, a modulation signal detection circuit 106 which receives the electrical signals from the photoelectric converting elements 105 and selectively detects modulation signals corresponding to irradiation positions (positions of top ends of the irradiation use optical fibers 103) and the wavelengths and a continuous variable amplifier 107.

As the photoelectric converting element 105, a photo multiplier can be used. Further, when the photo diode is used, an avalanche photo diode is preferable which can realize photo measurement in a high sensitivity. The modulation signal detection circuit 106 is one that selectively detects a modulation signal corresponding to an irradiation position and a wavelength and in a case of analog modulation, uses a lock-in amplifier. Further, in a case of digital modulation, such as a digital filter and a digital signal processor are used. Still further, in the present embodiment, since the lights having two wavelengths are used as the irradiation lights, the number of signals to be measured (number of measurement channels) is [measurement points]×[2], therefore, the same number of lock-in amplifiers as the number of signals has to be provided. The signals detected for every measurement channel are amplified by the continuous variable amplifier 107, are converted into digital signals by an A/D converter not shown and are sent to the signal processing unit 108.

The signal processing unit 108 is provided with a memory 109 which records signals from the photometer unit 105–107, a processing unit 110 which processes the signals from the photometer unit 105–107, calculates variation amount of hemoglobin in blood along time axis, extracts characteristics (indexes) of the variation amount of hemoglobin in blood along time axis and performs judgment whether normal health or any of diseases based on the extracted characteristics, a memory unit 111 such as a hard disk which stores the processed result by the processing unit 111 and data necessary for the processing and a data base in which characteristics of hemoglobin variation patterns for every disease are prepared as reference templates and a display unit 112 which displays a time course graph of measured hemoglobin signals and a topography image based on the processed result. Although not illustrated in the drawing, the signal processing unit 108 is further provided with an input unit for inputting conditions in the optical measurement and patient information. The signal processing unit 108 having such structure can be built in a general use personal computer, can be directly connected to the photo topography unit 101 via a cable or alternatively, the data exchange between them can be performed via such as a telecommunication network and a portable media.

Figure 2:
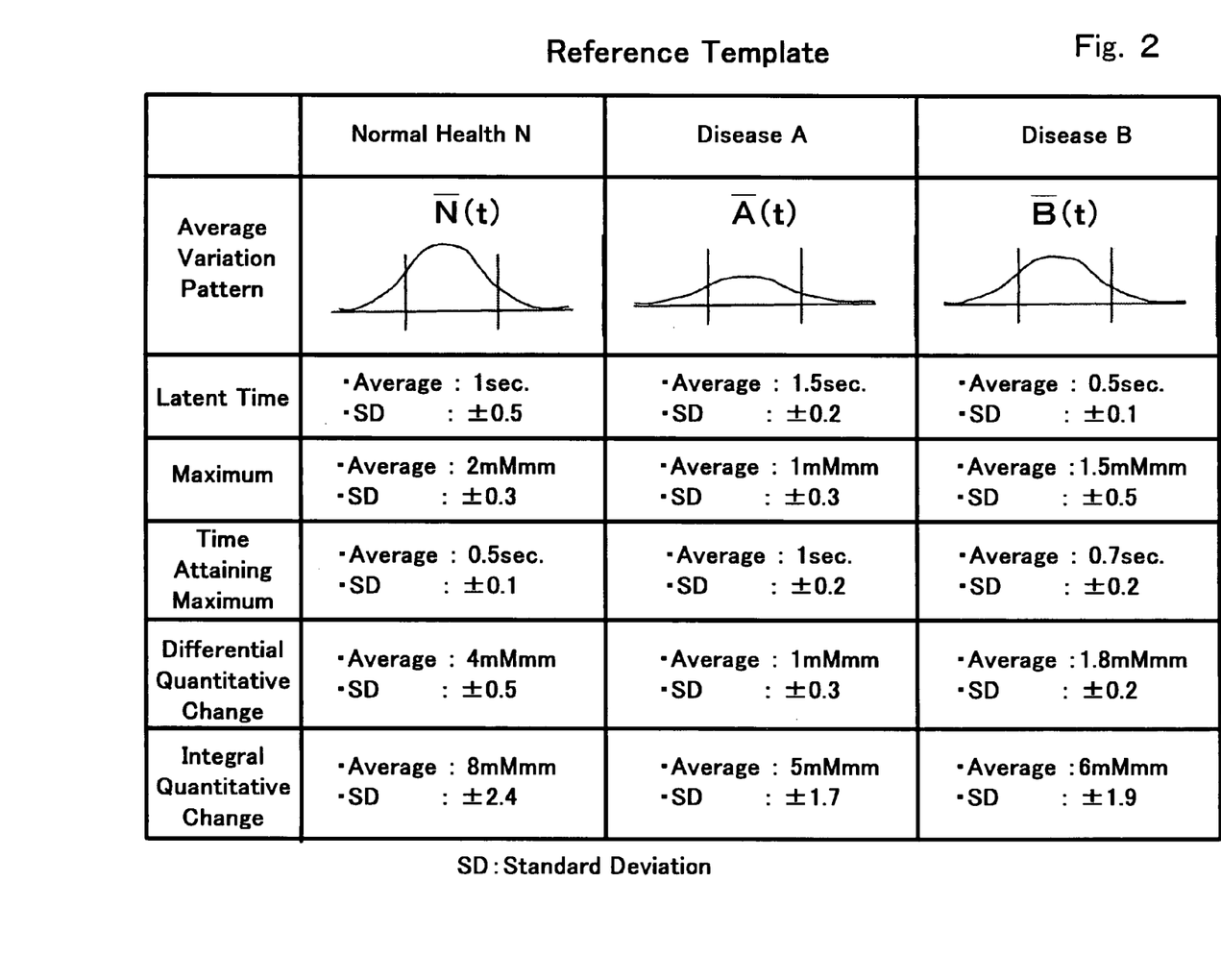
FIG. 2 is a view showing an example of a reference template of normal health, disease A and disease B, which is provided in a biological photometer according to the present invention.

FIG. 2 shows an example of database for normal health and diseases built in the memory unit 111 in a form of reference templates. In the illustrated embodiment, by making use of six items of indexes (characteristics) of average variation pattern in hemoglobin signal variation, latent time, maximum level, time for attaining the maximum level, differential quantitative change and integral quantitative change determined from the average variation patterns, reference templates for respective normal health and a variety of diseases are prepared and added into the database.

Such a database can be prepared by statistically processing hemoglobin variation signals measured in advance of normal health persons, patients of disease A and patients of disease B. As a method of extracting the indexes from the hemoglobin signal variation, for example, the method as disclosed in JP-A-2002-177281 which is a prior application applied by the same applicant of the present application can be used. Herein below, the disclosed method will be briefly explained.

Figure 3A:
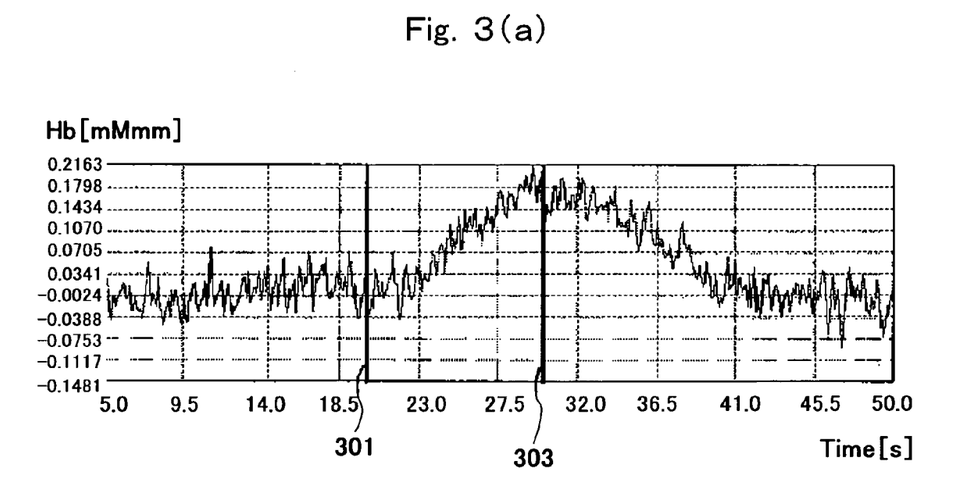
FIGS. 3(a) and 3(b) are views for explaining processing of a hemoglobin signal for preparing the reference template as shown in FIG. 2.
Figure 3B:
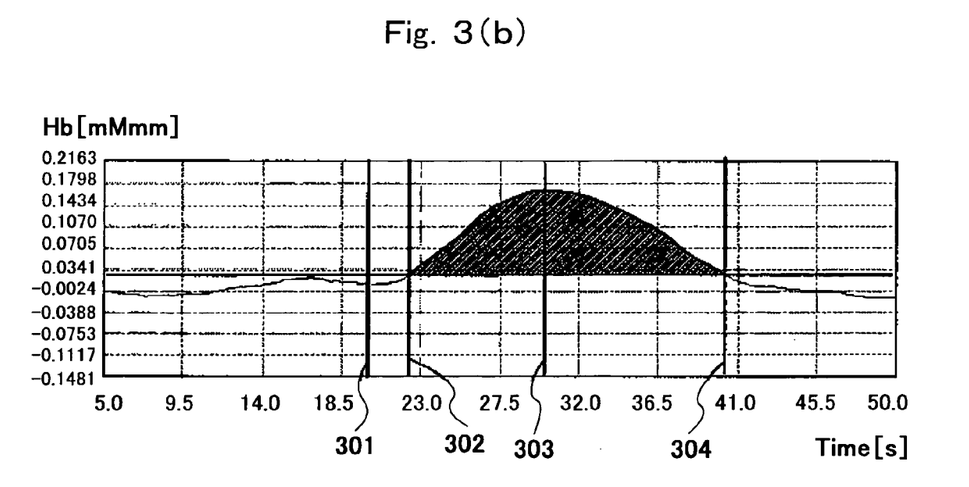

Under a condition where the attachment member 104 is attached to the subject, a predetermined task (for example, hand gripping motion) is given, while performing light irradiation and light receiving and the hemoglobin amount variation during that time is measured. The hemoglobin signal measured by the photometer unit in this instance contains noises as shown in FIG. 3(*a*). For this raw signal, a filtering process and base line process are applied and a curve as illustrated in FIG. 3(*b*) is obtained. From this obtained curve, the maximum level and a position where the hemoglobin level exceeds a threshold level (a position where hemoglobin density begins to vary after giving a task at time point 301), namely onset position can be determined, and the latent time defined by a time from the beginning of the task to the onset position and the time for attaining the maximum defined by a period from the onset position attaining to the maximum level can be calculated. Further, from this curve, the differential value (hemoglobin variation rate) of the hemoglobin variation curve which is determined by an inclination from the onset position 302 to a predetermined position and the integration value of the hemoglobin variation curve which is determined by an area from the onset position 302 to a predetermined position, namely a position 304 where the hemoglobin level lowers below the threshold level, are respectively obtained. Numeral 303 indicates a time point when the task is ended.

Figure 4:
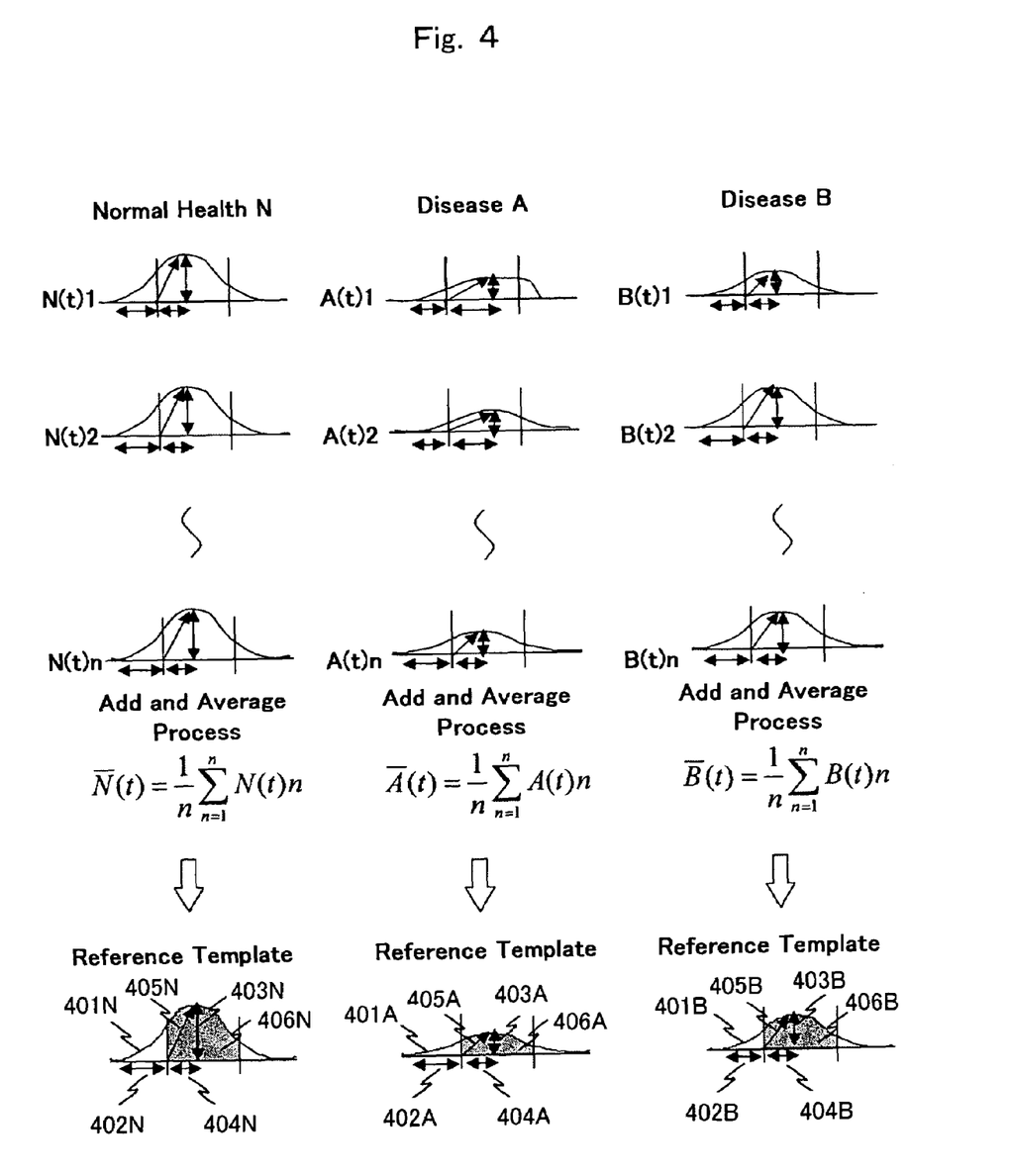
FIG. 4 is a view showing an example of steps for preparing the reference template as shown in FIG. 2.

FIG. 4 shows steps for preparing respective reference templates for normal health N, disease A and disease B. In the illustrated example, hemoglobin signals N(t)1–N(t)n, A(t)1–A(t)n and B(t)1–B(t)n of a plurality (n) of normal health persons and a plurality (n) of patients of each disease A and B are subjected to adding and averaging processing to prepare respective reference templates of variation patterns 401N, 401A and 401B as well as from the respective hemoglobin signals, the above referred to indexes are determined and after subjecting the determined indexes to adding and averaging processing, latent times 402N,402A and 402B, maximum levels 403N, 403A and 403B, times for attaining the maximum 404N, 404A and 404B, differential change values 405N, 405A and 405B and integral change values 406N, 406A and 406B of the reference templates are determined.

The indexes such as the latent time and maximum level which are kept as the reference templates can be obtained by determining the respective indexes from the time course data of hemoglobin signals of the plurality of patients and thereafter by subjecting the determined result to the adding and averaging processing as has been explained above, however, these can be obtained from the variation patterns determined by adding and averaging the time course data of hemoglobin signals.

Further, in FIG. 4, although a processing of the hemoglobin signal variation only at one measurement point (measurement channel) among a plurality of measurement points has been explained, the same processing is performed for the other measurement points. Still further, the respective indexes (latent time, maximum level, time for attaining the maximum, differential change value and integral change value) can be determined by adding and averaging the respective indexes at all of the measuring points, however, in a case of a disease when the hemoglobin variation is limited at a specific region, it is possible to determine the indexes by adding and averaging only hemoglobin signals at the measurement points covered by the specific region, moreover, it is possible to use indexes obtained at a specific one measurement point or alternatively, to use indexes determined by adding and averaging respective indexes at a plurality of specific measurement points. Thereby, a further accurate diagnosis can be performed.

As has been explained above, the reference templates can be prepared through an automatic calculation by making use of hemoglobin signals measured from subjects whose normal health, disease A or disease B is already known. In this instance, in order to enhance significance of the statistical processing, it is preferable to use measurement result of population as many as possible, for example, for every sexes and ages (adult and child). As another method of preparing reference templates, for example, hemoglobin signals of subjects are observed every time and according to the result of the observation, the above reference template preparation steps are performed separately for the respective subjects judged as normal health, disease A or disease B, and such process is continued to increase respective populations.

These reference template preparation steps can be executed by selecting the preparation steps from the input unit in the signal processing unit 108. The prepared reference templates are stored in the memory unit 111.

The above explained reference template preparation steps are functions for extracting indexes from the measured hemoglobin signals, and by making use of these functions indexes of a patient whose normal health or any of diseases is unknown are extracted from determined hemoglobin variation patterns of the patient and diagnosis is performed based no the extracted indexes.

Figure 5:
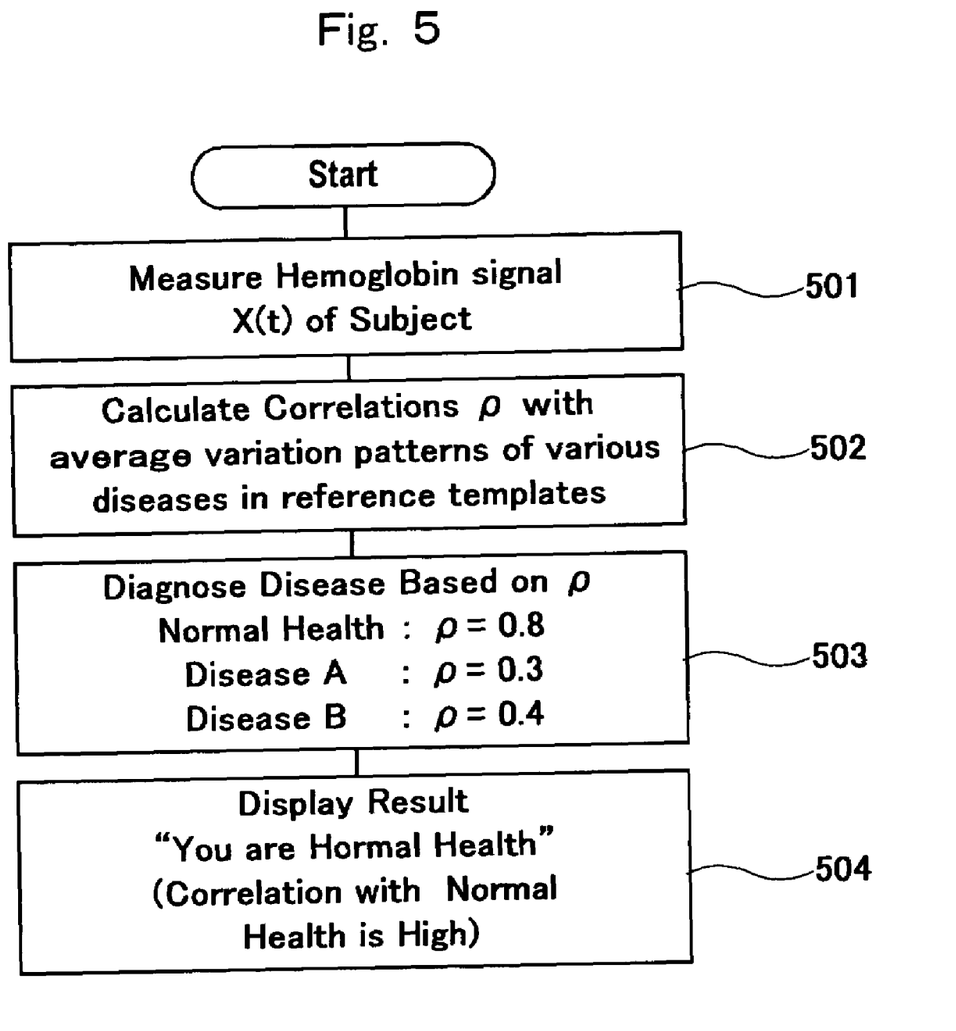
FIG. 5 is a flow chart showing an embodiment of diagnosis, which makes use of reference templates.

Herein below, steps of diagnosing any of diseases by making use of the reference templates will be explained. The diagnosis of diseases can be performed by making use of only the average variation pattern among indexes held as reference templates or alternatively can be performed by making use of indexes other than the average variation pattern. Further, the diagnosis can be performed by making use of any combinations of the average variation pattern with other indexes. FIG. 5 shows diagnosis processing steps, which make use of the average variation patterns in the reference templates.

At first, hemoglobin signal X (t) of a subject is measured (step 501). Subsequently, a correlation between the measured hemoglobin signal X(t) and the average variation patterns Y (N, A, B,) in the reference templates held in the database are searched (step 502). The correlation can be judged by calculating a correlation coefficient ρ as shown in the following equation;

$$\rho = \frac{C_{X(t)Y(t)}}{\sigma_{X(t)}\sigma_{Y(t)}}$$

$C_{X(t)Y(t)}$: codispersion value of X(t)Y(t)
$\sigma_{X(t)}$: dispersion value of X(t)
$\sigma_{Y(t)}$: dispersion value of Y(t)

Namely, the correlation coefficient $\rho(-1 \leq \rho \leq 1)$ possesses the following properties (1)~(3) and when the closer the correlation coefficient ρ between the measures hemoglobin signal X(t) and a certain average variation pattern Y(t) to 1, the higher the possibility of the subject being suffered to the disease having the certain average variation pattern.

(1) ρ=+1: When X(t) increases in positive correlation, Y(t) also increases.
(2) ρ=−1: When X(t) increases in negative correlation, Y(t) decreases.
(3) ρ=0: no correlation between X(t) and Y(t).

Accordingly, for example, all of the correlation coefficients ρ with respect to the average variation patterns in the reference templates of all of the diseases (including normal health, the same is true in the following) held in the database is determined, and then the subject is diagnosed as being suffered to the disease having the highest correlation. Alternatively, it is possible to diagnose that the subject suffers to a disease having a predetermined correlation value (for example, 0.8). In the example as shown in FIG. 5, the correlation is determined with respect to three average variation patterns of normal health N, disease A and disease B (step 503), and the state having the highest correlation 0.8 is judged as the state of the subject and the judgment result is displayed on the display unit 112 (step 504). In this instance, together with the diagnosis result, the reason of the diagnosis (because the correlation to normal health is most close to 1) can be displayed as illustrated. Alternatively, other than the final result obtained at step 504, correlations with the respective diseases (result at step 503) also can be displayed. Thereby, reliability of the final diagnosis result can be confirmed.

Figure 6:
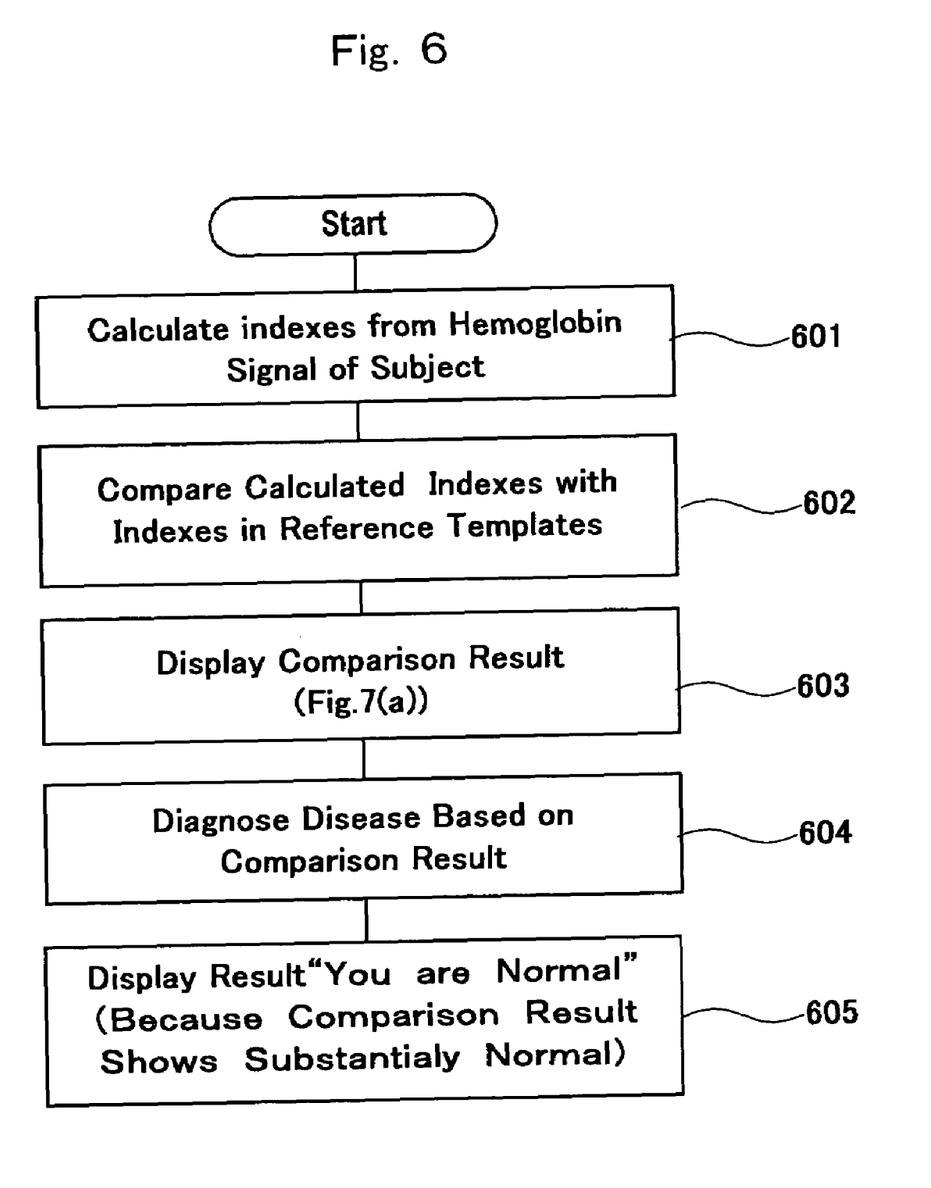
FIG. 6 is a flow chart showing another embodiment of diagnosis, which makes use of reference templates.

FIG. 6 shows other diagnosis processing steps, which make use of latent time 402, maximum level 403, time for attaining the maximum 404, differential change value 405 and integral change value 406. In this instance, as in the same manner when the reference templates are prepared, from the measured hemoglobin signals the latent time, maximum level, time for attaining the maximum, differential change value and integral change value of the measured hemoglobin signals are calculated (step 601). Subsequently, these calculated values are respectively compared with the latent time, maximum level, time for attaining the maximum, differential change value and integral change value of normal health and respective diseases in the reference templates (step 602).

Figure 7A:
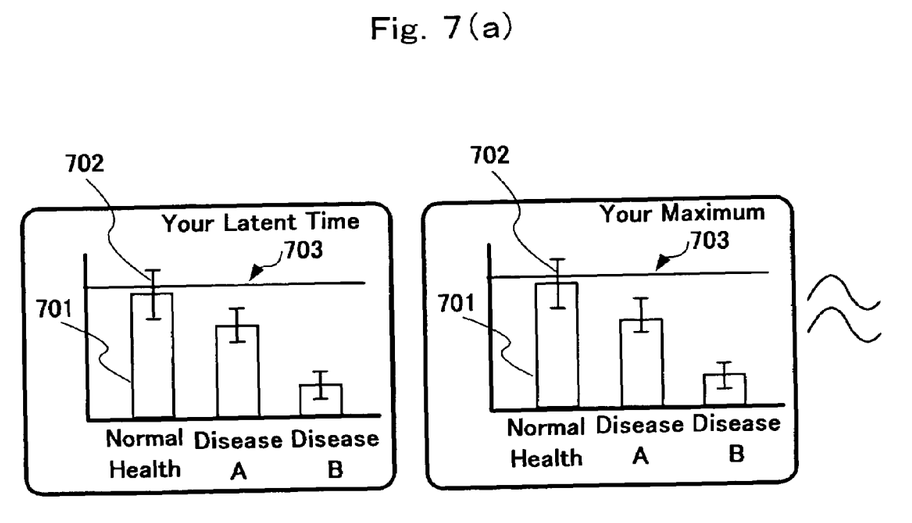
FIGS. 7(a) and 7(b) are views showing display examples in connection with the diagnosis steps as shown in FIG. 6.

In order to facilitate diagnosis, respective indexes 701 and their standard deviations 702 of normal health and respective diseases are displayed as well as the calculated values 703 of the subject are displayed in a superposed manner (step 603). The display examples are shown in FIG. 7(a). By means of such a display, the respective indexes and the calculated values of the subject can be grasped visually. Subsequently, it is determined for every one of the indexes to which disease the subject is close (step 604) In this step, for example, it is judged whether or not the maximum level in the hemoglobin amount variation of the subject is within the standard deviation in the reference template of a predetermined disease, and if within the standard deviation, the subject is judged being suffered to the disease. In the like manner, with respect to the other indexes, it is judged whether or not the indexes are within the standard deviations thereof. If any of the values of the subject drops within the standard deviations of normal health and any diseases, the subject can be judged to be normal health or any one of the diseases having the nearest value or alternatively, the judgment can be suspended.

Figure 7B:
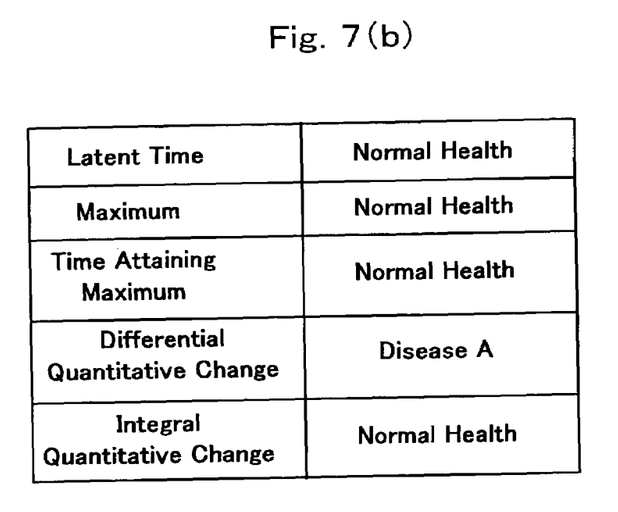

FIG. 7(b) shows such display example in which the judgment results for the respective indexes are displayed. Finally, the judgment results for the respective indexes are judged comprehensively (step 605). Namely, for example, if not less than 4 indexes among the 5 indexes indicate that the subject is suffered to a certain disease including normal health, it is judged that the subject is suffered to the disease. Namely, with respect to the example as shown in FIG. 7(b), since the subject is judged to be in normal health from the indexes other than the differential change value in step 604, the comprehensive diagnosis result is determined to be normal health for the subject. Further, for example, if not less than 3 indexes indicate that the subject is suffered to a certain disease, it is judged that the subject is suffered to the disease in high possibility.

In FIGS. 5 and 6, diagnosis using either the average variation pattern or indexes other than the average variation pattern is explained, however, the combination thereof can be used. Further, in parallel with the exemplary display in FIG. 7, an average variation pattern can be displayed.

According to the present embodiments as has been explained hitherto, the hemoglobin variation pattern and indexes are calculated from the measured hemoglobin signals as well as these calculated results are automatically compared with the hemoglobin variation pattern in the reference templates and indexes representing the characteristics thereof to perform diagnosis.

Herein above the embodiments of biological photometers according to the present invention have been explained, however, the present invention is not limited to the embodiments, but is adaptable to a variety of modifications. For example, as the indexes used for diagnosing diseases any proper combinations of the above five indexes can be used.

Further, in the above embodiments, although the preparation of the reference templates and the diagnosis function using the same have been explained, with the biological photometer according to the present invention, the hemoglobin variation in a measurement region can be displayed in a topographic image with contour lines in the same manner as conventional.

According to the biological photometer of the present invention, through the provision of the preparation function of reference templates which extract characteristics of normal health and a variety of diseases and diagnosis function using the same, quantitative diagnosis can be performed, thereby, diagnosis efficiency can be enhanced.

The invention claimed is:
1. A biological photometer comprising a light source which generates light being irradiated to a subject, a photometer unit which detects light transmitted inside the subject and produces a hemoglobin signal corresponding to hemoglobin density inside the subject, and a signal processing unit which prepares hemoglobin variation information of the subject based on the hemoglobin signal and displays the hemoglobin variation information, characterized in that the signal processing unit is provided with a memory unit which stores characteristics of hemoglobin variation patterns of respective normal health and a variety of diseases as reference templates, a characteristic extraction unit which extracts characteristics of a hemoglobin variation pattern of the subject based on the hemoglobin signal produced by the photometer unit, and a judgment unit which judges normal health or a kind of disease of the subject through comparison between the extracted characteristics of the hemoglobin variation pattern and respective reference templates of the normal health and the variety of diseases stored in the memory unit.

2. A biological photometer according to claim 1, characterized in that the characteristics of hemoglobin variation pattern includes at least one of a hemoglobin variation pattern curve, latent time, maximum level, time for attaining the maximum level, differential quantitative change and integral quantitative change determined from the curve.

3. A biological photometer according to claim 2, wherein the latent time is a period from beginning of a task to a moment when the hemoglobin signal exceeds a threshold value.

4. A biological photometer according to claim 2, wherein the time for attaining the maximum level is a period from a moment when the hemoglobin signal exceeds a threshold value to a moment when the hemoglobin signal attains the maximum level.

5. A biological photometer according to claim 2, wherein the integral quantitative change is an area determined by integrating the hemoglobin signal variation curve from a moment when the hemoglobin signal exceeds a threshold value to a moment when the hemoglobin signal drops below the threshold value.

6. A biological photometer according to claim 2, wherein the judgment unit determines whether the characteristics of the measured hemoglobin variation is within a standard deviation in the reference template of a predetermined disease and if within the standard deviation, is judged as the disease.

7. A biological according to claim 2, wherein, when a predetermined number of characteristics of hemoglobin variation among a plurality of characteristics of hemoglobin variation indicates a disease, the judgment unit judges the indicated disease as the disease.

8. A biological photometer according to claim 1, wherein the reference templates stored in the memory unit are prepared by statistically processing hemoglobin variation signals measured in advance of normal health persons and patients of the variety of diseases.

9. A biological photometer according to claim 1, wherein the reference templates stored in the memory unit are prepared by subjecting hemoglobin signals of a plurality of normal health persons and a plurality of patients of the variety of diseases to adding and averaging processing.

10. A biological photometer according to claim 9, wherein the characteristics of hemoglobin variation of the reference templates are determined from variation patterns of the hemoglobin signals after being subjected to the adding and averaging processing.

11. A biological photometer according to claim 9, wherein in a case of a disease when the hemoglobin variation is limited at a specific region, the characteristics of hemoglobin variation of the reference templates are determined by adding and averaging hemoglobin signals only from measurement points covered by the specific region.

12. A biological photometer according to claim 1, wherein the judgment unit judges a kind of disease based on a correlation between the measured hemoglobin signals and an average of the variation patterns of the reference templates stored in the memory unit.

13. A biological photometer according to claim 1, wherein the judgment unit determines correlations between the measured hemoglobin signals and an average of the variation patterns of the plurality of reference templates stored in the memory unit and judges a kind of disease based on a reference template having the highest correlation or a reference template having a predetermined value.

14. A biological photometer according to claim 1, wherein the signal processing unit displays a judgment result from the judgment unit.

15. A biological photometer comprising;
a light source unit which generates light having a predetermined wavelength in a region from visual to infrared;
an optical fiber which guides the light from the light source unit to a detection portion of a subject and irradiates the guided light thereto;
a photometer unit which detects light irradiated from the optical fiber and transmitted inside the subject and produces a hemoglobin signal corresponding to hemoglobin density at the detection portion of the subject; and
a signal processing unit which prepares a hemoglobin variation at the detection portion of the subject along a time axis based on the hemoglobin signal from the photometer unit and displays the hemoglobin variation, characterized in that,
the signal processing unit is provided with a characteristic extraction unit which extracts characteristics of a hemoglobin variation pattern based on the prepared hemoglobin variation at the detection portion of the subject, a memory unit which stores characteristics of hemoglobin variation patterns at the same detection portions of respective normal health and a variety of diseases in a form of reference templates, and a judgment unit which compares the characteristics of the hemoglobin variation pattern at the detection portion of the subject extracted by the characteristic extraction unit and the reference templates representing the characteristics of the hemoglobin variation patterns at the same detection portions of the respective normal health and variety of diseases stored in the memory unit and judges whether the subject is in normal health or in any one of the diseases.

16. A biological photometer according to claim 15, characterized in that the judgment unit judges whether the subject is in normal health or in any one of the diseases based on a comparison between at least one of latent time, maximum level, time for attaining the maximum, differential change value and integral change value of a hemoglobin variation pattern curve of the hemoglobin variation pattern at the detection portion of the subject extracted by the characteristic extraction unit and the characteristics corresponding to the reference templates of normal health and the variety of diseases at the same detection portions stored in the memory unit.

17. A biological photometer according to claim 16, wherein the latent time is a period from beginning of a task to a moment when the hemoglobin signal exceeds a threshold value.

18. A biological photometer according to claim 16, wherein the time for attaining the maximum level is a period from a moment when the hemoglobin signal exceeds a threshold value to a moment when the hemoglobin signal attains the maximum level.

19. A biological photometer according to claim 16, wherein the integral quantitative change is an area determined by integrating the hemoglobin signal variation curve from a moment when the hemoglobin signal exceeds a threshold value to a moment when the hemoglobin signal drops below the threshold value.

20. A biological photometer according to claim 16, wherein the judgment unit determines whether the characteristics of the measured hemoglobin variation is within a standard deviation in the reference template of a predetermined disease and if within the standard deviation, is judged as the disease.

21. A biological photometer according to claim 16, wherein, when a predetermined number of characteristics of hemoglobin variation among a plurality of characteristics of hemoglobin variation indicates a disease, the judgment unit judges the indicated disease as the disease.

22. A biological photometer according to claim 15, wherein the reference templates stored in the memory unit are prepared by statistically processing hemoglobin variation signals measured in advance of normal health persons and patients of the variety of diseases.

23. A biological photometer according to claim 15, wherein the reference templates stored in the memory unit are prepared by subjecting hemoglobin signals of a plurality of normal health persons and a plurality of patients of the variety of diseases to adding and averaging processing.

24. A biological photometer according to claim 23, wherein the characteristics of hemoglobin variation of the reference templates are determined from variation patterns of the hemoglobin signals after being subjected to the adding and averaging processing.

25. A biological photometer according to claim 23, wherein in a case of a disease when the hemoglobin variation is limited at a specific region, the characteristics of hemoglobin variation of the reference templates are determined by adding and averaging hemoglobin signals only from measurement points covered by the specific region.

26. A biological photometer according to claim 15, wherein the judgment unit judges a kind of disease based on a correlation between the measured hemoglobin signals and an average of the variation patterns of the reference templates stored in the memory unit.

27. A biological photometer according to claim 15, wherein the judgment unit determines correlations between the measured hemoglobin signals and an average of the variation patterns of the plurality of reference templates stored in the memory unit and judges a kind of disease based on a reference template having the highest correlation or a reference template having a predetermined value.

28. A biological photometer according to claim 15, wherein the signal processing unit displays a judgment result from the judgment unit.

29. A biological photometer comprising;
a light source unit which generates light having a predetermined wavelength in a region from visual to infrared;
an optical fiber which guides the light from the light source unit to a detection portion of a subject and irradiates the guided light thereto;
a photometer unit which detects light irradiated from the optical fiber and transmitted inside the subject and produces a hemoglobin signal corresponding to hemoglobin density at the detection portion of the subject; and
a signal processing unit which prepares a hemoglobin variation at the detection portion of the subject along a time axis based on the hemoglobin signal from the photometer unit and displays the hemoglobin variation, characterized in that,
the signal processing unit is provided with a characteristic extraction unit which extracts characteristics of a hemoglobin variation pattern based on the prepared hemoglobin variation at the detection portion of the subject, a memory unit which stores characteristics of hemoglobin variation patterns at the same detection portions of respective normal health and a variety of diseases in a form of reference templates, and a judgment unit which compares the characteristics of the hemoglobin variation pattern at the detection portion of the subject extracted by the characteristic extraction unit and the reference templates representing the characteristics of the hemoglobin variation patterns at the same detection portions of the respective normal health and variety of diseases stored in the memory unit and judges whether the subject is in normal health or in any one of the diseases;
characterized in that the judgment unit determines a correlation coefficient $\rho$ between a hemoglobin variation pattern curve of the hemoglobin variation pattern at the detection portion of the subject extracted by the characteristic extraction unit and a hemoglobin variation pattern curve in the reference templates of normal health and the variety of diseases at the same detection portions stored in the memory unit and judges whether the subject is in normal health or in any one of the diseases based on the determined correlation coefficient.

30. A biological photometer according to claim 29, wherein the signal processing unit displays correlations with respective diseases.

31. A biological photometer comprising a light source which generates light being irradiated to a subject, a photometer unit which detects light transmitted inside the subject and produces a hemoglobin signal corresponding to hemoglobin density inside the subject and a signal processing unit which prepares hemoglobin variation information of the subject based on the hemoglobin signal and displays the hemoglobin variation information, characterized in that the signal processing unit is provided with a memory unit which stores characteristics of hemoglobin variation patterns of respective normal health and a variety of diseases as reference templates, a characteristic extraction unit which extracts characteristics of a hemoglobin variation pattern of the subject based on the hemoglobin signal produced by the photometer unit, and a judgment unit which idles normal health or a kind of disease of the subject through comparison between the extracted characteristics of the hemoglobin variation pattern and the respective reference templates of the normal health and the variety of diseases stored in the memory unit;
characterized in that the signal processing unit modifies the reference templates at the same detection portions of the normal health and the variety of diseases stored in the memory unit by making use of the characteristics of the hemoglobin variation pattern at the detection portion of the subject extracted by the characteristic extraction unit and a judgment result by the judgment unit whether the subject is in normal health or any one of the diseases based on the characteristics.

32. A biological photometer comprising;

a light source unit which generates light having a predetermined wavelength in a region from visual to infrared;

an optical fiber which guides the light from the light source unit to a detection portion of a subject and irradiates the guided light thereto;

a photometer unit which detects light irradiated from the optical fiber and transmitted inside the subject and produces a hemoglobin signal corresponding to hemoglobin density at the detection portion of the subject; and a signal processing unit which prepares a hemoglobin variation at the detection portion of the subject along a time axis based on the hemoglobin signal from the photometer unit and displays the hemoglobin variation, characterized in that, the signal processing unit is provided with a characteristic extraction unit which extracts characteristics of a hemoglobin variation pattern based on the prepared hemoglobin variation at the detection portion of the subject, a memory unit which stores characteristics of hemoglobin variation patterns at the same detection portions of respective normal health and a variety of diseases in a form of reference templates, and a judgment unit which compares the characteristics of the hemoglobin variation pattern at the detection portion of the subject extracted by the characteristic extraction unit and the reference templates representing the characteristics of the hemoglobin variation patterns at the same detection portions of the respective normal health and a variety of diseases stored in the memory unit and judges whether the subject is in normal health or in any one of the diseases;

characterized in that the signal processing unit modifies the reference templates at the same detection portions of the normal health and the variety of diseases stored in the memory unit by making use of the characteristics of the hemoglobin variation pattern at the detection portion of the subject extracted by the characteristic extraction unit and a judgment result by the judgment unit whether the subject is in normal health or any one of the diseases based on the characteristics.

* * * * *